United States Patent [19]

Scholtz

[11] 4,265,639

[45] May 5, 1981

[54] COMBUSTION CATALYSTS

[76] Inventor: Myndert T. Scholtz, 2437 Edenhurst Dr., Mississauga, Ontario, Canada, L5A 2L2

[21] Appl. No.: 132,119

[22] Filed: Mar. 20, 1980

[51] Int. Cl.³ .............................................. C10L 1/22
[52] U.S. Cl. .......................................... 44/57; 44/68; 44/71
[58] Field of Search .............................. 44/68, 71, 57; 260/429 J

[56] References Cited

U.S. PATENT DOCUMENTS

| | | | |
|---|---|---|---|
| 2,506,539 | 5/1950 | Boardman | 44/68 |
| 3,282,858 | 11/1966 | Simmons et al. | 44/68 |
| 3,711,525 | 1/1973 | Hennart | 260/43 |
| 3,758,534 | 9/1973 | Popper et al. | 260/439 R |
| 3,833,590 | 9/1974 | Dazzi | 260/439 R |
| 4,145,190 | 3/1979 | Webb | 44/57 |

*Primary Examiner*—Winston A. Douglas
*Assistant Examiner*—Y. Harris-Smith
*Attorney, Agent, or Firm*—Cushman, Darby & Cushman

[57] ABSTRACT

The present invention relates to a stabilized, combustion promoting fuel additive containing an iron (II) chelate and a picric acid/organic base complex. The invention further relates to stock solutions containing this additive, methods for producing the additive and fuels containing the additive.

15 Claims, No Drawings

COMBUSTION CATALYSTS

The present invention relates to a stabilized fuel additive, solutions comprising the additive, methods for producing the additive and fuels comprising the additive.

There has been considerable interest in developing new combustion catalyst systems for use with gasoline, diesel and residual oil fuels. The use of an effective combustion catalyst may result in the following advantages:

(i) improvement in the fuel economy;
(ii) reduction of hydrocarbon and carbon monoxide emissions;
(iii) reduction of carbon formations; and
(iv) for an oil fired plant, a reduction in excess air requirement leading to an increased efficiency.

While combustion catalysts may have broad application for all liquid hydrocarbon fuels, the present invention primarily relates to the development of combustion catalysts for gasoline and diesel fuels.

In automobile engines, combustion characteristics of a fuel/air mixture largely determines the nature of flame propogation which to a great extent determines the engine power output. Autoignition can be minimized by using antiknock compounds as tetraethyl-lead (TEL) or methyl cyclopentadienyl manganese tricarbonyl (MMT). Both TEL and MMT interfere with the operation of catalytic converters in the automobile exhaust system and their use in unleaded gas has been banned by the United States Environmental Protection Agency.

Recently developed refining techniques can produce unleaded gasoline with high anti-knock characteristics. It should be noted, however, that these gasolines or the use of anti-knock compounds does not necessarily give the most efficient combustion characteristics from the point of view of the engine's pressure-volume cycle.

The function of the anti-knock compounds is not exactly known. However, there are indications that they reduce the detonation tendency of the end gas (see for example, Polss, P., (1973) Hydrocarbon Proc. 52(2) p. 61–68).

As with the function of TEL as an anti-knock agent, the mechanism of combustion catalysts is not well understood. For oil fired boilers, combustion catalysts generally comprise organometallic compounds of metals such as manganese, calcium, barium and cobalt. In order to be effective for heavy oil combustion, the metal concentration must be of the order of 27 ppm. At this level, combustion efficiency is increased and the excess air to the combustion chamber may be reduced without smoke formation so increasing the fuel economy of the instalation. Reduction of soot deposits on the heat transfer surfaces improves heat transfer and lowers the stack-gas temperature, further increasing efficiency. Efficiency increases of from 3 to 6% may result from the use of combustion catalyst, and for a poorly maintained installation much higher increases are possible. With heavy oil combustion, it is likely that the action of a combustion catalyst is to simply increase the rate of combustion by direct catalytic effect ensuring more complete combustion with less excess air.

Combustion catalysts used in conjunction with internal combustion engines are unlikely to be as simple in function. There is very little to be found in the literature on the function of these combustion catalysts. Some work is in progress in the Soviet Union as evidenced by recent publications, e.g., Maiko, L. P., E. P. Seregin, M. O. Lerner, L. A., Aleksandrova, V. I. Petrof, V. T. Bugai (1977) Chem. Technol. Fuels and Oils, 13 (3–4), p 253–256. The function of combustion catalysts for internal combustion engines is likely similar to those for heavy fuel oil in that they modify the rate of combustion of the fuel/air mixture. This modification likely results in a more favorable pressure-volume cycle within the cylinder in order to result in an increase in efficiency. Hence, unlike anti-knock compounds which apparently operate in the end-gas zone, combustion catalysts likely modify the combustion characteristics of the fuel/air mixture to give improved flame front propogation.

Some information on catalysts or combustion aids for internal combustion engines is obtained from the Chemical Abstracts or other publications such as Ranney, M. W., (ed), (1975) Fuel Additives for internal combustion engines, Recent Developments. Chem. Technol. Review No. 112. Some combustion aids are used in such large concentrations that they qualify more as blending components rather than catalysts or additives. Some combustion catalysts contain organometallic compounds in small amounts. The resulting concentration of metal in the fuel is generally less than 0.1 ppm compared to about 500 ppm for anti-knock compounds. Other formulations contain compounds which modify the combustion characteristics of the fuel/air mixture by altering the chemical mechanisms which lead to the oxidation of the hydrocarbons. The actual process of oxidation is very complex and proceeds via many intermediate chemical species. Commonly used compounds in combustion aids are organic peroxides and nitro compounds. The performance of combustion catalysts for internal combustion engines is claimed to vary from several percent fuel savings to as much as 25%. It is clear from the manner in which the combustion catalysts are thought to function, that the advantages of use are going to depend on the particular engine, its state of tuning or adjustment, internal cleanliness and factors of design. An engine which is inherently very efficient has a lesser potential for improvement compared to an inefficient engine. From published test results and the patent literature it appears that claimed fuel savings average about 15%.

In connection with the aforementioned problems associated with the combustion of fuels, a two component catalytic additive for fuels has been proposed having iron in the $+2$ valence state as one component and picric acid or a picrate radical as the other component, U.S. Pat. Nos. 3,282,858 (Simmons et al); 4,073,626 (Simmons); 4,099,930 (Webb); 4,129,421 (Webb); and 4,145,190 (Webb). Solutions of these components are often green, due to the presence of iron (II) picrate. However, iron (II) picrate has been found to be relatively unstable in fuels such as gasoline. For instance, when a green solution of iron (II) picrate is added to gasoline, a brown coloration may be obtained immediately upon such addition. While not wishing to be bound to any particular mechanism for the formation of such a brown coloration, this change in color may be attributed to a reaction between iron (II) picrate and additives in the gasoline. Furthermore, the iron component of iron (II) picrate is prone to the formation of gums or precipitates in storage tanks possibly due to the presence of even small amounts of water condensed in the fuel or contained in the additive solvent mixture.

Accordingly, there is a need in the art to develop additives having enhanced stability.

The present invention relates to fuel additives which promote the combustion of fuels. While these additives are particularly useful in gasoline and diesel fuels, they may also be used to promote combustion in other fuels such as jet fuel, domestic heating oil, light industrial oil, and residual or bunker fuel.

The additives of the present invention include active catalytic ingredients, as well as stabilizing ingredients. Active, catalytic ingredients are iron in the +2 valence state and picric acid or picrate. Accordingly, the active, catalytic ingredients of the present additive and their use in fuels are known. Thus, one of ordinary skill in the art could readily select proper amounts and proportions of these ingredients for use in fuels. Furthermore, particular amounts and proportions of these ingredients are set forth hereinbelow. However, before discussing these particular parameters, it should be noted that the acidic hydrogen atom of picric acid in organic solution may be fully attached to the picrate radical or partially or totally removed therefrom. Therefore, for the purposes of the present specification and the claims which follow the expression "picric acid" shall connote free picric acid as well as picrate, whether the picric acid is present in the protonated or deprotonated form.

The additive should preferably contain at least about a stoichiometric amount of picric acid with respect to the iron component of the additive. In other words, the additive may contain at least about a 2:1 molar ratio of picric acid with respect to iron in the +2 valence state. Accordingly, the molar ratio of picric acid to iron may be between about 2:1 to about 550:1, more particularly, about 2:1 to about 200:1, about 140:1 being preferred. Optionally, excess picric acid over a 2:1 molar ratio with respect to iron may be at least partially replaced by at least one aromatic or aliphatic nitro compound such as nitroaliphatic compounds having 1 to 4 carbon atoms, trinitrophenols other than picric acid, trinitrocresols and picramic acid.

The additives of the present invention further comprise an EDTA chelating agent and an amine. While not wishing to be bound by any particular theory or mechanism, the enhanced stability of the additives of the present invention would seem to be largely or at least partially attributable to the ability of the stabilizing ingredients to prevent the formation of iron (II) picrate in solutions and/or fuels containing the additives. More particularly, the iron component of the catalyst would seem to be tied-up by EDTA and picric acid would seem to be tied-up by the amine, such that the iron and picric acid are maintained in a separated fashion in solution. This separation of iron and picric acid in solution may be evidenced by an absence of the green color characteristic of iron (II) picrate.

It is noted that the composite molecular structure formed by the interaction of amine with picric acid shall be referred to herein as a complex. Thus, for the purposes of the present specification and the claims which follow, reference to a picric acid/amine complex shall connote any composite molecular structure formed by the interaction of the amine with the picric acid through the acidic hydrogen of picric acid, regardless of the degree of dissociation of this hydrogen from the picric acid. Therefore, picric acid/amine salts are encompassed within the meaning of picric and/amine complexes.

It is also noted that the amine component of the additive may further function to enhance the solubility of the EDTA chelating agent. Therefore, there would seem to be a dual advantage in utilizing an amine in accordance with the present invention.

The additives of the present invention should include a stabilizing amount of an EDTA chelating agent for the iron (II) component and a stabilizing amount of an amine complexing agent for the picric acid component. The amine complexing agent should also have sufficient solubility and complexing characteristics to form a soluble picric acid/amine complex in the stock solutions and the fuels of the present invention. Particular amines are primary secondary or tertiary monoamines of the formula

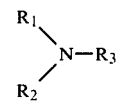

where $R_1$, $R_2$ and $R_3$ are hydrocarbyl groups having 1 to 12 carbon atoms, and more particularly 2 to 8 carbon atoms, or hydrogen, provided that the amine contains at least 3 carbon atoms. Amines containing 12 or less carbon atoms are preferred. These hydrocarbyl groups may be fully aliphatic or aromatic in character or they may have both aliphatic and aromatic constituents. Aliphatic groups or constituents may be saturated or unsaturated and may be characterized as having a straight-chain, branched-chain or cyclic structure. Particular amines include cyclohexylamine, 2-ethylhexylamine, n-propylamine, n-butylamine, triethylamine, diethylamine, dicyclohexylamine and aniline, cyclohexylamine being preferred.

The amount of EDTA should preferably be sufficient to form an iron (II)/EDTA chelate with all of the +2 iron present in the additive. This amount may be characterized as a chelating amount. Similarly, a complexing amount of an amine is an amount which is sufficient to form a picric acid/amine complex with essentially all of the picric acid present in the additive.

Excess amounts of EDTA and/or amines are wasteful and may present problems, e.g., with respect to the solubility thereof. Accordingly, it is preferable to use a minimum effective amount of these agents such as a 1:1 molar ratio of EDTA to iron and a 1:1 molar ratio of amine to picric acid. It is observed in many cases that an amine to picric acid ratio in excess of that required to form the complex leads to precipitation of the complex in certain solvents such as iso-propyl alcohol. Precipitation may be avoided by maintaining a slight excess acidity through addition of picric acid or other organic acids. On the other hand, if a large excess of picric acid is present over that required to completely complex with the amine, the formation of green ferrous picrate is observed in many cases with some solvents.

The choice of solvent or solvent mixture has some importance since the solubility of the picric acid/organic base complex will vary for different solvent systems. For example, an excess of organic base will not lead to precipitation of the picric acid complex in methanol as was observed in iso-propanol.

Accordingly, when the additive of the present invention is prepared as a relatively concentrated stock solution which may subsequently be added in small portions to fuels, some care must be taken in choosing solvents which are compatible with each of the components of the additive. Examples of solvents which may be compatible with the components of the additive include toluene, xylene, methanol, ethanol, isopropyl alcohol, butanol, aromatic petroleum fractions and mixtures thereof.

Stock solutions containing from about 1.01 to about 0.20 g of iron in the +2 valence state per liter of stock solution, preferably 0.06 g/l, may be added to gasoline or diesel fuel in a part-to-part ratio of 1:1000 to 1:2000, about 1:1600 being preferred. Accordingly, gasoline and diesel fuels may contain from about 0.005 to about 0.20 mg of the iron constituent of the additive per liter of fuel. Bunker and residual fuels generally contain larger amounts of the additive than gasoline or diesel fuels. Possible sources of +2 iron include ferrous sulfate and ferrous carbonate.

According to one method aspect of the present invention, additives may be prepared by the steps of (i) combining EDTA and amine in a suitable solvent such as methanol; (ii) adding picric acid to a suitable solvent such as methanol to make a solution of picric acid; (iii) adding a source of +2 iron to the picric acid solution of step (ii) with stirring to obtain a green iron picrate solution; and (iv) adding portions of the solution of step (i) to the green iron picrate solution of step (iii) with agitation until the green color disappears and a clear yellow solution is obtained. The color change of step (iv) is rapid, taking place immediately upon sufficient addition of the solution of step (i).

According to yet another method aspect of the present invention, additives may be prepared by the steps of (i) combining EDTA and amine in a suitable solvent such as methanol; (ii) dissolving picric acid in the solution of step (i); and (iii) adding a source of +2 iron to the solution of step (ii) with stirring to give a red orange solution which on standing (e.g., without stirring for about 12 to 100 hours) goes to a clear yellow solution.

According to a further method aspect of the present invention, additives may be prepared by (i) combining EDTA and amine in a suitable solvent such as methanol; (ii) adding a +2 iron source to the solution of step (i) with stirring to get a chelated iron solution; and (iii) adding a picric acid solution to the solution of step (ii) to get a clear yellow solution.

According to yet another method aspect of the present invention, additives may be prepared by the steps of (i) combining said EDTA and said amine in a methanol solution; (ii) adding picric acid to the solution of step (i) and dissolving; (ii) adding a source of +2 iron to the solution of step (ii) and stirring to suspend and dissolve to give a red orange solution; and (iv) adding isopropyl alcohol to the solution of step (iii) to obtain a clear organic solution which goes yellow upon standing (e.g., without stirring for about 12 to 100 hours).

The additives of the present invention exhibit good stability in fuels such as gasoline. There is no evidence of side reactions taking place among these additives and gasoline and/or other additives in gasoline. Side reactions are undesirable, because they negate the effect of other additives and increase the rate of deterioration of the gasoline on storage through oxidation or other breakdown. Furthermore, reaction of an additive with gasoline likely leads to loss of effectiveness of the combustion catalyst.

Fuel comprising the additive of the present invention is stabilized with respect to the formation of gums or precipitates over a period of time due to the presence of moisture. Accordingly, gasoline, for example, when treated with these additives, has the essential stability necessary to maintain its catalytic effectiveness over prolonged periods whether in bulk storage or in automobile tanks.

EXAMPLE 1

Preparative Method 1

EDTA (8 g) and cyclohexylamine (100 g) was dissolved in methanol (96 ml) to give a stock solution. In a separate container picric acid (1.0 g, including approximately 0.15 g of water present in the picric acid as purchased) was dissolved in methanol (100 ml) to form a picric acid/methanol solution. $FeSO_4.7H_2O$ (0.03 g) was then added to the picric acid/methanol solution and was dissolved with stirring to obtain a green iron (II) picrate solution. Finally, approximately 0.96 ml of the EDTA/cyclohexylamine/methanol stock solution was added with agitation to the green iron (II) picrate solution until the green color disappeared and a clear yellow solution was obtained.

EXAMPLE 2

Preparative Method 2

EDTA/cyclohexylamine/methanol and picric acid/methanol solutions are prepared in accordance with the procedure of Example 1. Next the EDTA/cyclohexylamine/methanol solution (0.96 ml) is added to the picric acid/methanol solution to form a combined solution. Finally, $FeSO_4.7H_2O$ (0.03 g) is added with stirring to this combined solution to give a red orange solution which on standing goes to a clear yellow solution.

EXAMPLE 3

Preparative Method 3

An EDTA/cyclohexylamine/methanol stock solution is formed in accordance with the procedure of Example 1. Approximately 0.96 ml of this stock solution is diluted by adding same to 10 ml of methanol. To this diluted solution is added $FeSO_4.7H_2O$ (0.03 g) with stirring to get a chelated iron solution. Finally, a picric acid/methanol solution (100 ml, 0.85 g/100 ml) is added to the chelated iron solution to get a clear yellow solution.

EXAMPLE 4

Preparative Method Using A Solvent Containing Iso-Propanol

An EDTA/cyclohexylamine/methanol stock solution is formed in accordance with the procedure of Example 1. Approximately 0.86 ml of this stock solution is added to 10 ml of methanol. Picric acid (1.0 g includes 15% water) is added to this solution and dissolved followed by $FeSO_4.7H_2O$ (0.03 g) which is dissolved with agitation to give a dark red/orange solution. To this solution is added 90 ml of iso-propyl alcohol to give a clear orange solution which goes yellow after several days. The final solution which contains a slight excess of picric acid is acidic. Should a precipitate form, this can be re-dissolved by the addition of a slight excess of picric acid. It is noted that the additive solution of Example 4 is particularly adaptable to diesel fuel, whereas the additive solutions of Examples 1, 2 and 3 are not, because methanol is only sparingly soluble in diesel fuel. However, the additive solutions of Examples 1, 2, 3 and 4 are each suitable for use in gasoline.

EXAMPLE 5

Additive Stability in Gasoline

Gasoline containing 650 ppm of a solution having a 1:140:6.4:80 ratio of iron: picric acid: EDTA: cyclohexylamine, the concentration of the solution being 60.3 mg/l with respect to iron, is prepared. The gasoline takes on a pale yellow color imparted by the additive which is yellow. There is no significant color change and no visible evidence of precipitation, gum formation or other breakdown of either the gasoline or combustion catalyst after several weeks of observation. When this gasoline is refluxed for one hour, there is again little evidence of significant breakdown. When this gasoline is exposed to trace amounts of water there is relatively little visible evidence of precipitation or other deterioration in either the gasoline or the combustion catalyst, even after several weeks.

COMPARATIVE EXAMPLE A

Gasoline is prepared in an identical manner as Example 5 except that both the EDTA and the cyclohexylamine of the additive are omitted. The green iron (II) picrate additive immediately changes color upon addition to the gasoline and the gasoline takes on a brown coloration upon such addition. Upon storage of this treated gasoline in a closed bottle for several weeks in a darkened cupboard a brown/green deposit is adhered to the glass at the bottom of the container. In the presence of light the formation of gummy deposits and precipitated material occurs more rapidly.

COMPARATIVE EXAMPLE B

Gasoline is prepared in an identical manner as Example 5 except that the picric acid is the only additive. The gasoline initially takes on the yellow coloration of the additive. However, after the gasoline was stored in a cupboard for one week, a brown coloration was observed.

EXAMPLE 6

Performance Tests

A stock solution of the additive was prepared in accordance with Example 1 and was mixed with unleaded gasoline in a ratio of 1 oz. per 12.5 U.S. gallons (i.e., 1 ml per 1.6 liters). A detailed description of the tests that were performed shows that virtually all variables have been taken into account.

Six cars consisting of matched pairs of 1979 two-door Toyota Corollas; 1979 four-door Pontiac Bonnevilles and 1979 Ford Thunderbirds were utilized in the test. The evaluation was performed under actual driving conditions on the road.

A unique adaptation of U.S. Department of Transportation procedure was utilized throughout these tests. Essentially, it measures fuel consumed on a weight rather than volume basis. This procedure is known for both its simplicity and repeatability. In the trade, it is known as a Type II RCC/SAE/DOT test.

The table below describes the vehicles which were tested.

VEHICLES TESTED:

| # | Make | Model | Engine | Milage | Weight |
|---|------|-------|--------|--------|--------|
| 1 | 1979 Pontiac | Bonneville 4 dr. | V-8 | 17,606 | 3,900 lbs. |
| 2 | 1979 Pontiac | Bonneville 4 dr. | V-8 | 17,849 | 3,975 lbs. |
| 3 | 1979 Ford | Thunderbird 2 dr. | V-8 | 22,636 | 4,200 lbs. |
| 4 | 1979 Ford | Thunderbird 2 dr. | V-8 | 22,690 | 4,200 lbs. |
| 5 | 1980 Toyota | Corolla 4 dr. | I-4 | 2,721 | 2,400 lbs. |
| 6 | 1980 Toyota | Corolla 4 dr. | I-4 | 2,384 | 2,400 lbs. |

At the conclusion of the test, cars were examined to determine the following:
1. Possible signs of a cleanup effect.
2. An assurance that the additive was not producing any negative effect on internal engine parts.

Inspection of Car #3 revealed no harmful effects from the additive of the present invention on the valve, piston, or head area.

In order to have a basis of comparison, the heads from Car #4 were also removed. Since Car #3 and Car #4 were virtually identical, the additive tested vehicle was compared to the non-additive tested vehicle. Analysis of Car #4 revealed no problems. Thus, both cars looked virtually identical. As a consequence of the positive results achieved, testing was extended for two more days, i.e., one day each for highway and simulated city cycle.

Overall, the results of these tests demonstrated an increase in miles per gallon in the range of 4% attributable to the use of the additive of the present invention. The additive was found to be effective at both speeds of 35 and 55 miles per hour. During the 35 mile per hour segment prearranged stops were part of the cycle. This included idling periods of up to one minute and acceleration and deceleration at stop lights, shopping center parking lots, and other specifically designated points. All vehicles traveled the identical route.

While certain representative embodiments and details have been shown for the purpose of illustrating the invention, it will be apparent to those skilled in the art that various changes and modifications may be made therein without departing from the spirit and scope of the invention. It will further be understood that the invention may comprise, consist essentially of or consist of the steps or materials recited herein.

What is claimed is:

1. A stabilized fuel additive consisting essentially of (i) an iron (II)/EDTA chelate and (ii) a complex of picric acid with at least one amine of the formula

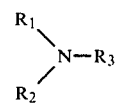

wherein $R_1$, $R_2$ and $R_3$ are hydrocarbyl groups having 1 to 12 carbon atoms, or hydrogen, provided that said amine has at least 3 carbon atoms.

2. In a fuel additive comprising (i) iron in the +2 valence state and (ii) picric acid, the improvement wherein said additive further comprises (iii) a chelating amount of EDTA sufficient to form an iron (II)/EDTA chelate with essentially all of the +2 iron present in said additive and (iv) a complexing amount of at least one amine sufficient to form picric acid/amine complex with essentially all of the picric acid present in said additive, wherein said amine is of the formula

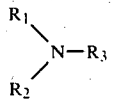

where $R_1$, $R_2$ and $R_3$ are hydrocarbyl groups having 1 to 12 carbon atoms, or hydrogen, provided that said amine has at least 3 carbon atoms.

3. An additive according to claim 2, wherein said hydrocarbyl groups represented by $R_1$, $R_2$ and $R_3$ have 2 to 8 carbon atoms, and said amine has 3 to 12 carbon atoms.

4. An additive according to claim 2, wherein the molar ratio of said EDTA to iron is approximately 1:1 and the molar ratio of said amine to picric acid is approximately 1:1.

5. A fuel additive solution comprising (i) about 0.01 to about 0.20 g of iron in the +2 valence state per liter of said solution, (ii) picric acid, wherein the molar ratio of said picric acid to said iron is from about 2:1 to about 550:1; (iii) a chelating amount of EDTA; (iv) a complexing amount of at least one amine of the formula

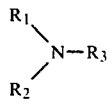

where $R_1$, $R_2$ and $R_3$ are hydrocarbyl groups having 1 to 12 carbon atoms, or hydrogen, provided that said amine has at least 3 carbon atoms; and (v) organic solvent which is compatible with said additive.

6. A solution according to claim 5, wherein said amine is selected from the group consisting of cyclohexylamine, 2-ethylhexylamine, n-butylamine, n-propylamine, triethylamine, diethylamine, dicyclohexylamine and aniline.

7. A method for preparing a fuel additive comprising (a) an iron (II)/EDTA chelate and (b) a complex of picric acid with at least one amine of the formula

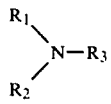

where $R_1$, $R_2$ and $R_3$ are hydrocarbyl groups having 1 to 12 carbon atoms, or hydrogen, provided that said amine has at least 3 carbon atoms, said method comprising the steps of:
(i) combining said EDTA and said amine in a methanol solution;
(ii) adding picric acid to methanol to make a solution of picric acid in methanol;
(iii) adding a +2 iron source to said picric acid solution of step (ii) with stirring to obtain a green iron (II) picrate solution; and
(iv) adding portions of said solution (i) to said green iron (II) picrate solution of step (iii) with agitation until the green color disappears and a clear yellow solution is obtained.

8. A method for preparing a fuel additive comprising (a) an iron (II)/EDTA chelate and (b) a complex of picric acid with at least one amine of the formula

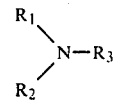

where $R_1$, $R_2$ and $R_3$ are hydrocarbyl groups having 1 to 12 carbon atoms, or hydrogen, provided that said amine has at least 3 carbon atoms, said method comprising the steps of:
(i) combining said EDTA and said amine in a methanol solution;
(ii) adding picric acid to methanol to make a solution of picric acid in methanol;
(iii) adding said picric acid solution of step (ii) to said solution of step (i); and
(iv) adding a +2 iron source to said solution of step (iii) with stirring to give a red orange solution which on standing goes to a clear yellow solution.

9. A method for preparing a fuel additive comprising (a) an iron (II)/EDTA chelate and (b) a complex of picric acid with at least one amine of the formula

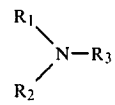

where $R_1$, $R_2$ and $R_3$ are hydrocarbyl groups having 1 to 12 carbon atoms, or hydrogen, provided that said amine has at least 3 carbon atoms, said method comprising the steps of:
(i) combining said EDTA and said amine in a methanol solution;
(ii) adding a +2 iron source to said solution of step (i) with stirring to get a chelated iron solution; and
(iii) adding a picric acid/methanol solution to said solution of step (ii) to get a clear yellow solution.

10. A method for preparing a fuel additive comprising (a) an iron (II)/EDTA chelate and (b) a complex of picric acid with at least one amine of the formula

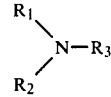

where $R_1$, $R_2$ and $R_3$ are hydrocarbyl groups having 1 to 12 carbon atoms, or hydrogen, provided that said amine has at least 3 carbon atoms, said method comprising the steps of:
(i) combining said EDTA said amine in a methanol solution;
(ii) adding picric acid to the solution of step (i) and dissolving;
(iii) adding a source of +2 iron to the solution of step (ii) and stirring to suspend and dissolve to give a red orange solution; and
(iv) adding isopropyl alcohol to the solution of step (iii) to obtain a clear orange solution which goes yellow upon standing.

11. A fuel comprising the additive of claims 1, 2, 3, or 4.

12. Gasoline comprising the additive of claims 1, 2, 3, or 4.

13. Diesel fuel comprising the additive of claims 1, 2, 3, or 4.

14. Gasoline comprising (i) about 0.005 to about 0.20 mg of iron per liter of said gasoline, (ii) picric acid, wherein the molar ratio of said picric acid to said iron is from about 2:1 to about 550:1; (iii) a chelating amount of EDTA; and (iv) a complexing amount of at least one amine of the formula

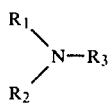

where $R_1$, $R_2$ and $R_3$ are hydrocarbyl groups having 1 to 12 carbon atoms, or hydrogen, provided that said amine has at least 3 carbon atoms.

15. Diesel fuel comprising (i) about 0.005 to about 0.20 mg of iron per U.S. gallon of said diesel fuel, (ii) picric acid, wherein the molar ratio of said picric acid to said iron is from about 2:1 to about 550:1; (iii) a chelating amount of EDTA; and (iv) a complexing amount of at least one amine of the formula

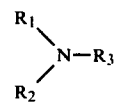

where $R_1$, $R_2$ and $R_3$ are hydrocarbyl groups having 1 to 12 carbon atoms, or hydrogen, provided that said amine has at least 3 carbon atoms.

* * * * *